United States Patent
Bron

(10) Patent No.: US 12,390,121 B2
(45) Date of Patent: Aug. 19, 2025

(54) IN-BORE VERTICAL HEIGHT ADJUSTMENT OF PATIENT AUTONOMY

(71) Applicant: KONINKLIJKE PHILIPS N.V., Eindhoven (NL)

(72) Inventor: Ben Bron, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 295 days.

(21) Appl. No.: 17/942,206

(22) Filed: Sep. 12, 2022

(65) Prior Publication Data

US 2023/0087137 A1    Mar. 23, 2023

Related U.S. Application Data

(60) Provisional application No. 63/246,038, filed on Sep. 20, 2021.

(51) Int. Cl.
| | | |
|---|---|---|
| A61B 5/055 | (2006.01) | |
| A61B 5/00 | (2006.01) | |
| A61B 6/04 | (2006.01) | |
| A61G 13/02 | (2006.01) | |
| A61G 13/12 | (2006.01) | |

(52) U.S. Cl.
CPC .............. *A61B 5/055* (2013.01); *A61B 5/704* (2013.01); *A61B 6/04* (2013.01); *A61B 6/0407* (2013.01); *A61B 6/0487* (2020.08); *A61G 13/02* (2013.01); *A61G 13/12* (2013.01)

(58) Field of Classification Search
CPC ........... A61B 5/055; A61B 5/704; A61B 6/04; A61B 6/0407; A61B 6/0487; A61G 13/02; A61G 13/12
See application file for complete search history.

(56) References Cited

U.S. PATENT DOCUMENTS

| | | | | |
|---|---|---|---|---|
| 4,914,682 | A * | 4/1990 | Blumenthal | A61B 6/0487 378/208 |
| 6,640,364 | B1 * | 11/2003 | Josephson | A61B 5/704 5/601 |
| 6,928,672 | B2 * | 8/2005 | Pastyr | A61B 6/0407 5/601 |
| 7,360,949 | B2 * | 4/2008 | Izuhara | A61B 6/4405 5/601 |
| 8,692,213 | B2 * | 4/2014 | Abenaim | A61B 6/0407 5/81.1 R |
| 10,335,096 | B2 * | 7/2019 | Nett | A61G 1/02 |
| 10,555,707 | B2 * | 2/2020 | Cohen | A61B 6/0464 |
| 2004/0057557 | A1 * | 3/2004 | Nafstadius | A61B 6/04 378/209 |
| 2007/0143921 | A1 * | 6/2007 | Hiyama | A61B 5/055 5/601 |
| 2015/0114404 | A1 * | 4/2015 | Czop | A61B 46/10 128/856 |
| 2017/0120078 | A1 * | 5/2017 | Payne | A61N 7/00 |

(Continued)

*Primary Examiner* — Myles A Throop

(57) ABSTRACT

A patient transfer system (10) for an imaging device (1) comprises: a bridge (12) disposed in a bore (5) of the imaging device; a bed (20) disposed adjacent the imaging device and having a bed extension (22) extending underneath the bridge; and a bed support pedestal (24) providing motorized height adjustment of the bed. Motorized operation of the bed support pedestal to raise the bed also lifts the bridge using the bed extension which extends underneath the bridge.

18 Claims, 8 Drawing Sheets

(56) References Cited

U.S. PATENT DOCUMENTS

2018/0031649 A1    2/2018  Harvey et al.
2022/0192603 A1*   6/2022  Zink .................. A61B 5/704
2023/0273281 A1*   8/2023  Weiss ................. G06T 7/70
                                                 324/309

* cited by examiner

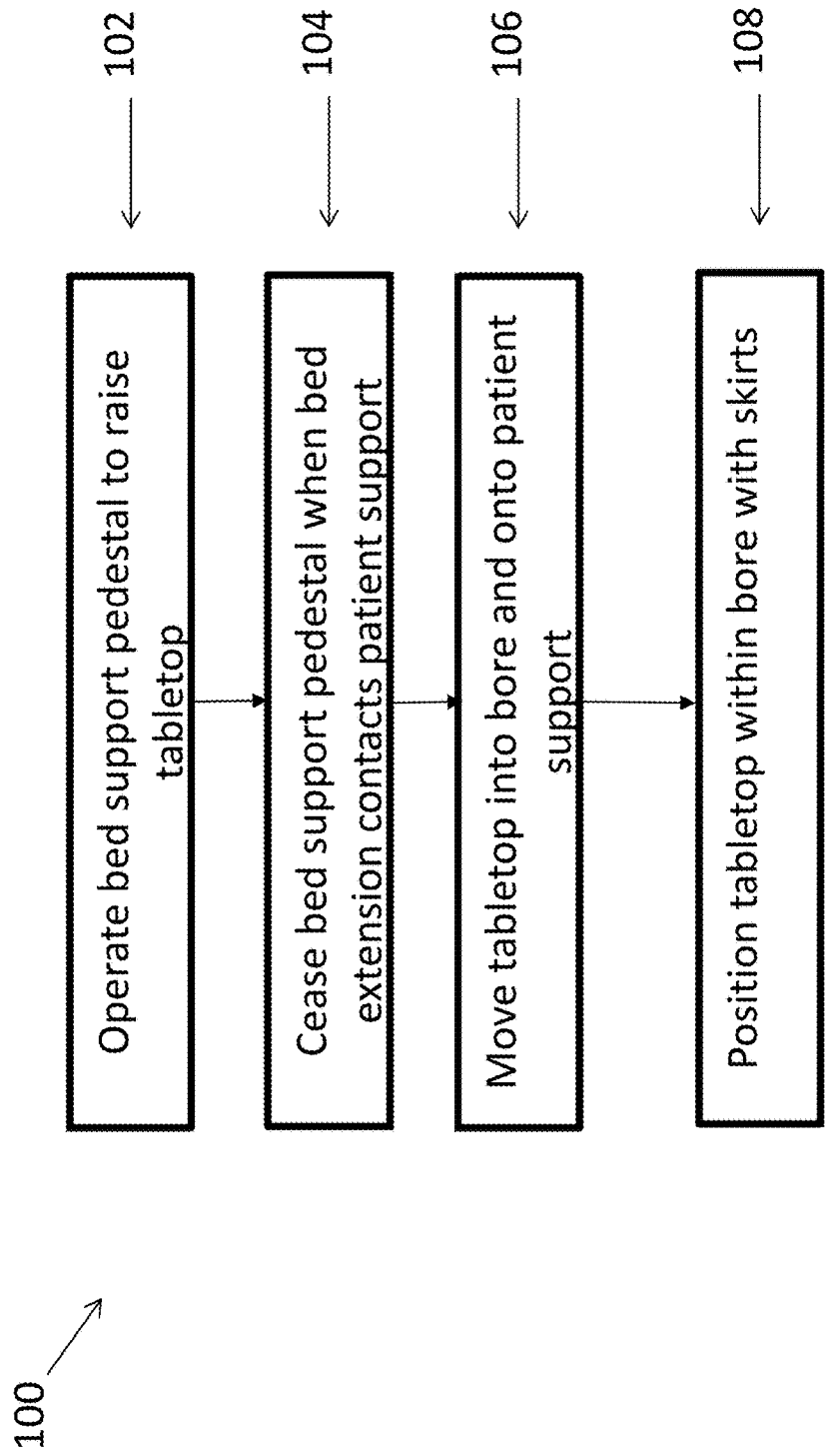

IN-BORE VERTICAL HEIGHT ADJUSTMENT OF PATIENT AUTONOMY

CROSS REFERENCE TO RELATED APPLICATION

This patent application claims the priority benefit under 35 U.S.C. 119(e) of U.S. Provisional Application No. 63/246,038 filed Sep. 20, 2021, the contents of which are herein incorporated by reference.

FIELD

The following relates generally to the magnetic resonance (MR) imaging arts, MR patient positioning arts, MR patient adjustment arts, and related arts.

BACKGROUND

Magnetic resonance (MR) imaging entails placing a subject (e.g., medical patient, veterinary subject, archaeological mummy, et cetera) in a static magnetic field (often referred to as a $B_0$ field) and exciting nuclear magnetic resonance in the subject and then detecting the excited magnetic resonance. For imaging, the excited MR is spatially encoded with respect to location, phase, and/or frequency by superimposing magnetic field gradients on the static $B_0$ magnetic field during the excitation, during a time interval between MR excitation and MR readout, and/or during the MR readout. In a typical design, the MR imaging device (sometimes referred to as an MRI scanner) includes a housing with a central bore within which the MR examination region is located. The static $B_0$ magnetic field is produced by solenoidal magnet windings wrapped around the central bore and housed within the MM scanner housing. These solenoidal magnet windings are often superconducting windings in modern MRI scanners, and the housing includes a liquid helium (LHe) reservoir cooling the superconducting windings. Magnetic field gradient coils are also disposed in the housing around the central bore.

A patient support of a typical MRI system typically facilitates vertical displacement of a tabletop (also referred to herein as a patient table) on which a patient is placed while the patient table is outside the bore tube. Such vertical displacement is intended to allow the tabletop to be lowered to facilitate movement of the patient from a gurney onto the tabletop, after which the patient table is vertically raised to align the tabletop with a table support surface or structure inside the bore. After the vertical alignment, the tabletop (with the patient thereon) is rolled or slid horizontally from the patient support outside the bore onto the table support surface or structure inside the bore. The vertical height of the tabletop inside bore in relation to magnet iso-center is typically fixed. With the introduction of wide bore cylindrical MRI systems, the vertical height of the tabletop inside the bore is typically fixed at a height which maximizes the bore space above the table, so as to accommodate patients of a widely varying size range. Obesity rates are often high in industrialized countries, for example the National Center for Health Statistics recently estimated the obesity rate in the United States to be nearly 40%, and this percentage is predicted to continue to rise. Given this prevalence, the support surface or structure of a wide bore MM is often designed for large patients. For large patients, a fixed table height can be selected which places anatomy like the spine at magnet iso-center height. This is particularly advantageous in enabling the largest imaging FOV for sagittal and coronal scans of the spine, and also enables handling of patients of a wide range of sizes. For patients of normal or slightly overweight size, however, the tabletop height in the bore which is designed for large patients can be too low for certain types of imaging, such as spinal imaging in which the patient is in the supine position (i.e., the patient positioned lying on his or her back and facing upward). In this case, the vertical height of the spine of the normal or slightly overweight patient is significantly lowered with respect to the magnet iso-center height. This leads to sub-optimal imaging coverage and potential effects such as compromised fat suppression.

Providing a height adjustment for the surface or structure inside the bore that supports the tabletop can resolve this issue. However, such height adjustment typically entails adding additional actuators and additional sensors to the MRI system, inside the bore, which adds to system complexity. Such additional actuators and sensors must be operable in the presence of high static and time-varying magnetic fields generated inside the bore.

Additionally, providing actuator-controlled height adjustment inside the bore adds complexity to the patient transfer process, because with this modification both tabletop height outside the bore and inside the bore are adjustable. That is, whenever the height of the surface or structure inside the bore that supports the tabletop is adjusted this in turn requires an adjustment of the aligned height of the tabletop that is to be set using the patient support disposed outside the bore, so as to provide level horizontal transfer of the patient. In current MRI systems, installation of the patient support needs quite accurate alignment (i.e., ±1 mm) in the vertical direction to enable a smooth transfer of the tabletop carrier from the patient support onto the bridge. Next to this, the magnet of the MM system is known to lower slightly over time due to its fixation on the floor. This means the misalignment tends to increase over time.

The following discloses certain improvements to overcome these problems and others.

SUMMARY

In some embodiments disclosed herein, a patient transfer system for an imaging device comprises: a bridge disposed in a bore of the imaging device; a bed disposed adjacent the imaging device and having a bed extension extending underneath the bridge; and a bed support pedestal providing motorized height adjustment of the bed. Motorized operation of the bed support pedestal to raise the bed also lifts the bridge using the bed extension which extends underneath the bridge.

In some embodiments disclosed herein, a patient transfer system for an imaging device includes: a bed disposed adjacent the imaging device; a bed support pedestal providing motorized height adjustment of the bed; a tabletop rollable or slidable between the bed disposed adjacent the imaging device and a bore of the imaging device; a mechanical linkage configured to adjust a height of a patient on the tabletop in the bore of the imaging device; and a motor operatively connected to operate the four-bar linkage.

In some embodiments disclosed herein, an imaging method includes: operating a bed support pedestal to raise a bed disposed adjacent an imaging device; and ceasing the operating of the bed support pedestal when a bed extension extending underneath a bridge disposed in a bore of the imaging device contacts a portion of the bridge.

One advantage resides in providing an MRI system with a vertically adjustable tabletop while the tabletop is also in a bore of the MRI system.

Another advantage resides in an MM system with a mechanism to automatically align an in-bore horizontal guidance with a horizontal guidance situated on a patient support in front of the MM system.

Another advantage resides in an MM system with a mechanism to automatically align an in-bore horizontal guidance without the need for additional actuators and sensors.

Another advantage resides in reducing a misalignment between the patient support relative to the bridge.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIG. 8 shows a flow chart of operations of an imaging method using the patient transfer system of FIG. 1.

DETAILED DESCRIPTION

Figure 1:
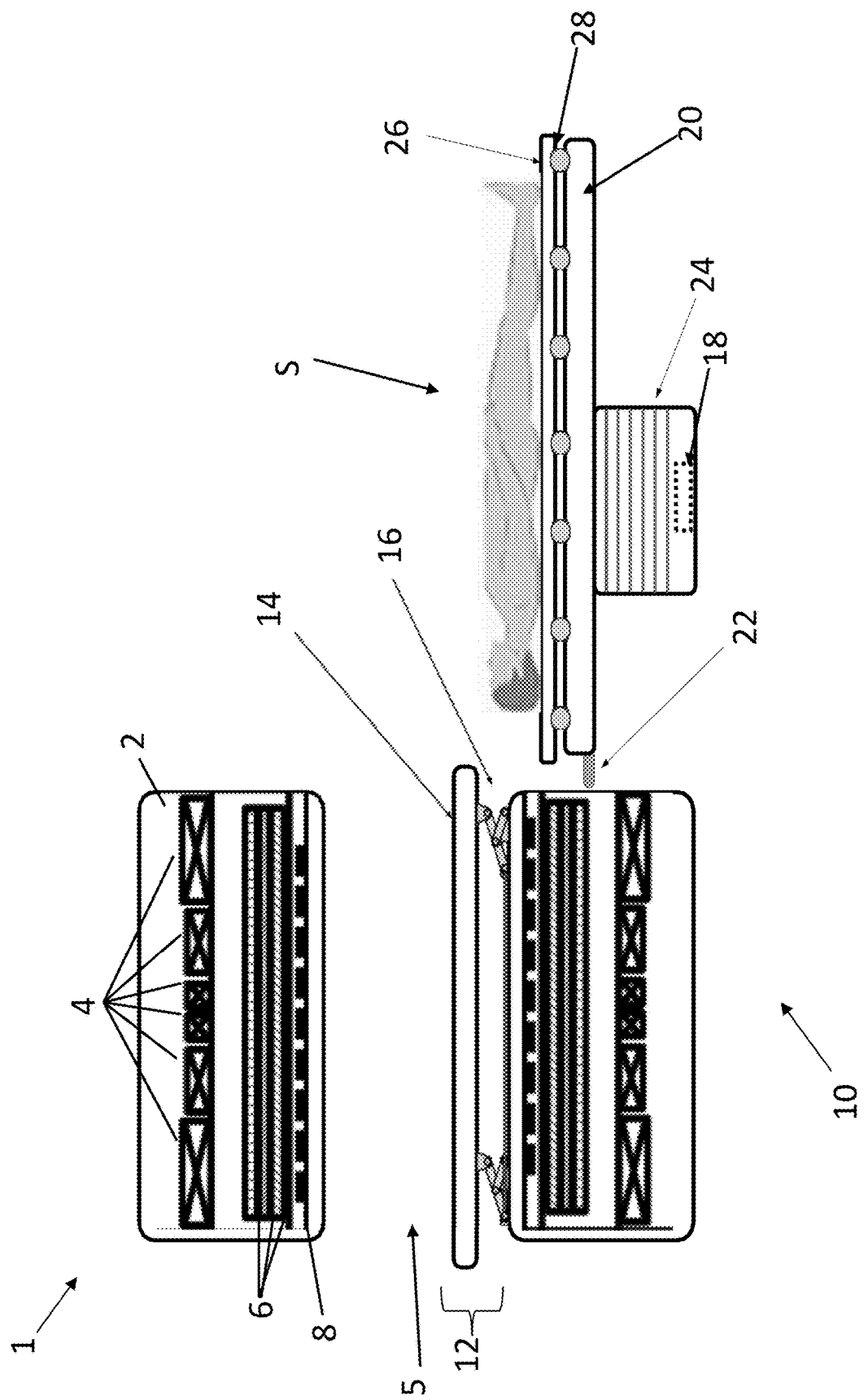
FIG. 1 diagrammatically illustrates a magnetic resonance (MR) imaging device including a patient transfer system in accordance with the present disclosure.

With reference to FIG. 1, an illustrative magnetic resonance (MR) imaging system or device 1 for imaging a subject S (e.g., an illustrative human subject S such as a medical patient, or a veterinary subject, or an archaeological mummy, et cetera) comprises a magnetic resonance (MR) imaging scanner (also referred to herein as an MRI scanner), which in the illustrative example includes a housing or gantry 2 containing various components shown in FIG. 1, such as by way of non-limiting illustrative example a superconducting or resistive magnet 4 generating a static ($B_0$) magnetic field, magnetic field gradient coils 6 for superimposing magnetic field gradients on the $B_0$ magnetic field, a whole-body radio frequency (RF) coil 8 for applying RF pulses to excite and/or spatially encode magnetic resonance in an imaging patient disposed in an MR bore 5 or other MR examination region, and/or so forth. The magnet 4 and the gradient coils 6 are arranged concentrically about the bore 5.

As shown in FIG. 1, the MR system 1 includes a patient transfer system 10 for loading the subject S into the bore 5. Disposed within the bore 5 is a bridge 12 that includes a patient support 14 and a mechanical linkage 16 securing the patient support 14 in the bore 5 (i.e., the mechanical linkage 16 is attached to a portion of the housing 2 that defines the bore 5). In some embodiments, the mechanical linkage 16 can be a Scott Russell linkage (e.g., having three bars with a slider at the bottom at a connection joint between the three bars). The Scott Russell linkage 16 allows for vertical movement of the patient support 14. The sliding joints of the Scott Russell linkage 16 are connected with each other via a pull rod to enable the patient support 14 to stay parallel with the bore 5.

As further shown in FIG. 1, the patient transfer system 10 includes a bed 20 disposed adjacent the MR device 1, and includes a bed extension 22 configured to extend underneath the bridge 12 (i.e., underneath the patient support 14). A bed support pedestal 24 provides motorized height adjustment of the bed 20. On top of the bed is a tabletop 26 that is rollable or slidable, via a set of wheels 28, between the bed 20 and the bridge 12.

Figure 2:
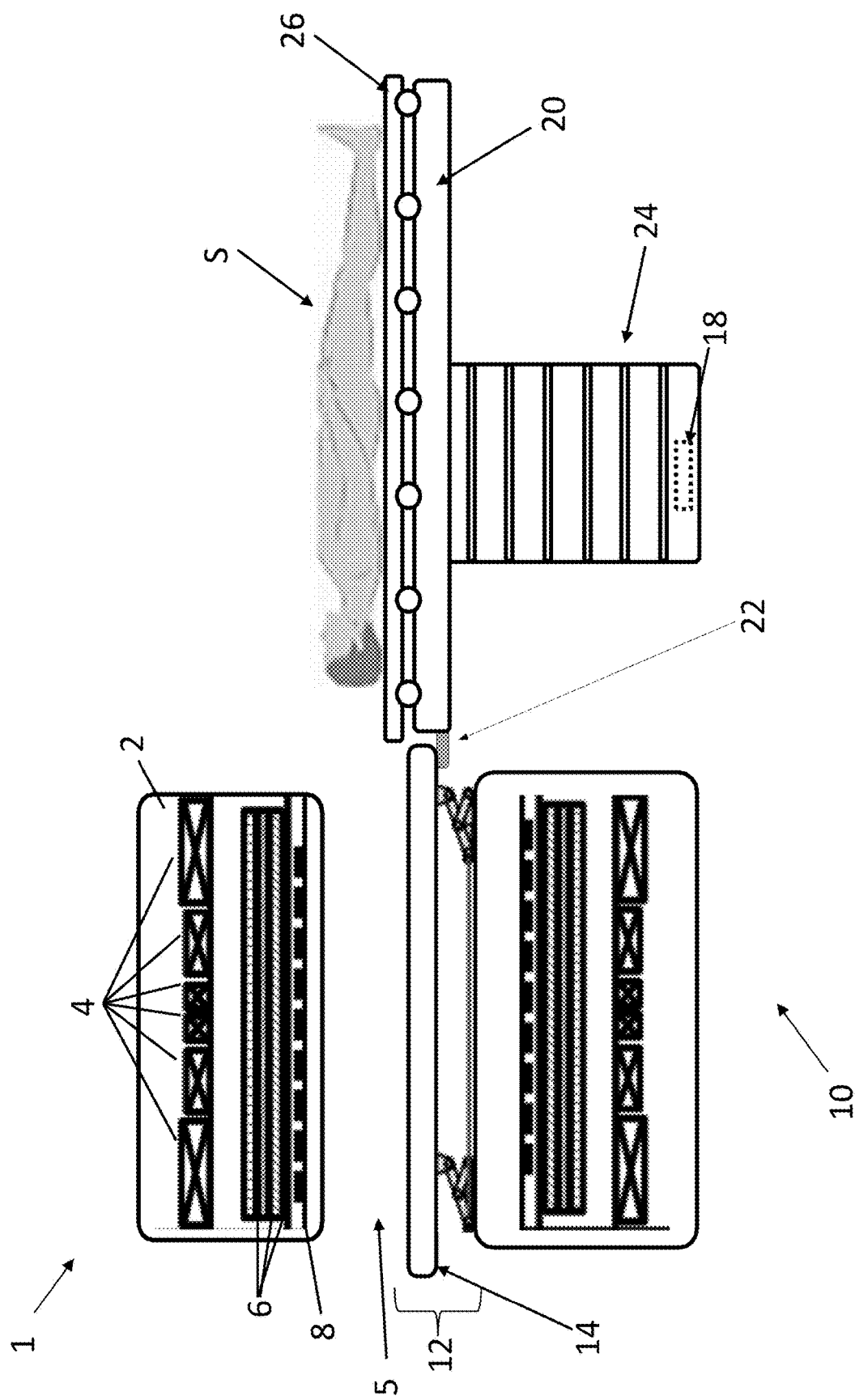
FIGS. 2 and 3 show different stages of motion of the patient transfer system of FIG. 1.
Figure 3:
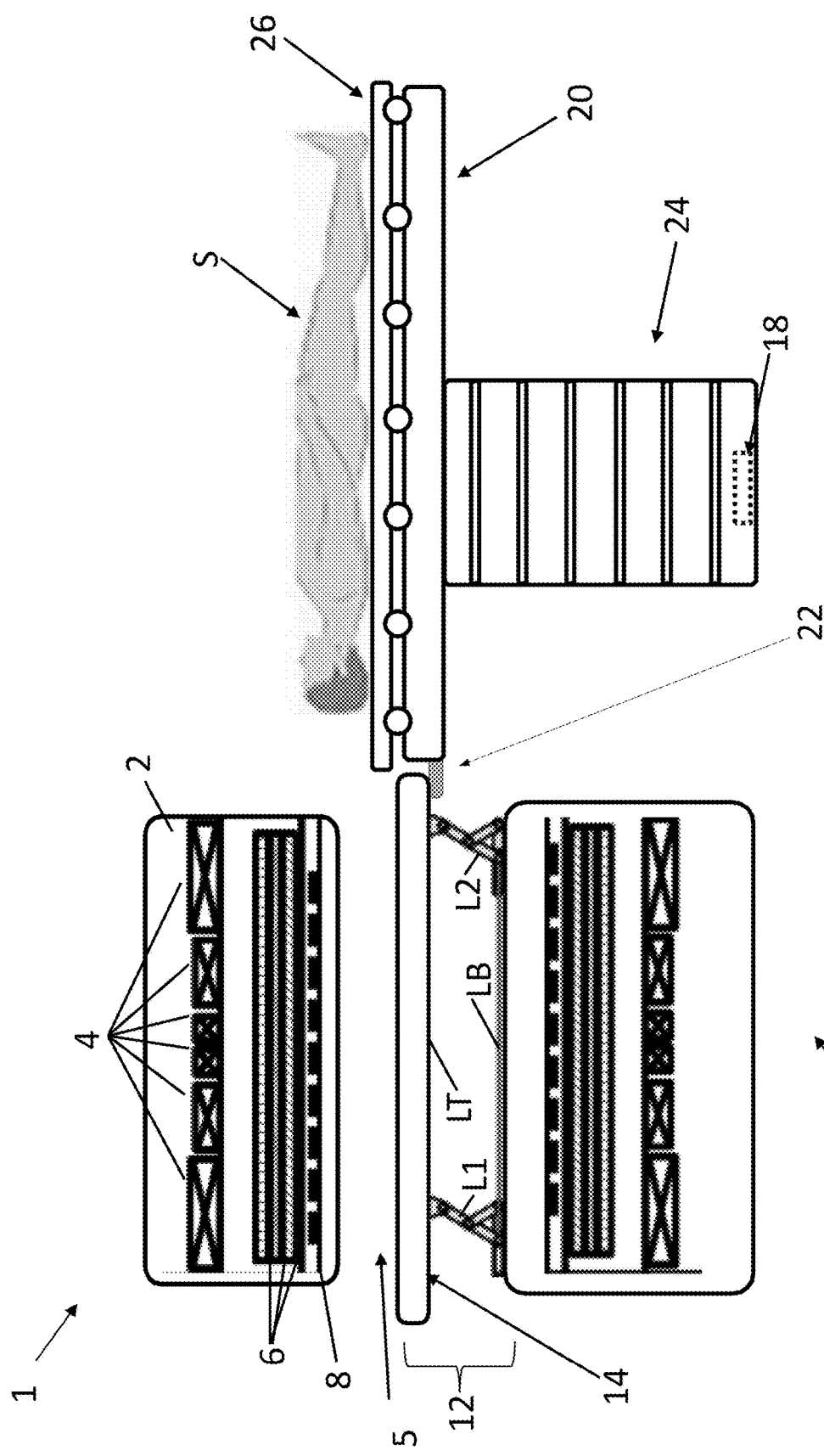

FIG. 1 shows the MR system 1 and the patient transfer system 10 before motorized operation of bed support pedestal 24 to raise the tabletop 26 (and thus the subject S) at a colinear level with the bridge 12. FIG. 2 shows that, after motorized operation of the bed support pedestal 24, the bed support pedestal 24 is raised vertically, thereby moving the tabletop 26 and the subject S vertically. As shown in FIG. 2, the bed extension 22 contacts or engages a bottom surface of the patient support 14. FIG. 3 shows further motorized operation of the bed support pedestal 24 (i.e., after the bed extension 22 contacts or engages the bottom surface of the patient support 14), the bed support pedestal 24 continues to be raised vertically, while also raising the bridge 12 via the engagement of the bed extension 22 with the patient support 14. Movement of the mechanical linkage 16 allows for vertical movement of the patient support 14. In some embodiments, the bridge 12 does not include a motor, while in other embodiments, the bridge 12 includes a motor 18 which can operate to further raise the patient support 14 via the mechanical linkage 16. Once the tabletop 26 is aligned (both horizontally and vertically) with the bridge 12, the tabletop 26 can be rolled from the bed 20 onto the patient support 14, thereby positioning the subject S in the bore 5 for imaging.

Advantageously, the mechanical linkage 16 ensures the vertically upward movement of the patient support 14 occurs in a manner in which the patient support 14 remains horizontal. Such level operation is inherent in the mechanics of a parallelogram four-bar linkage. As best seen (and labeled) in FIG. 3, the mechanical linkage 16 includes two riser elements forming two sides L1 and L2 of a parallelogram. The two sides L1 and L2 are of equal length, and have bottom ends secured by hinges to the bore 5 and top ends secured by hinges to (the bottom of) the patient support 14. The remaining two sides of the parallelogram of the mechanical linkage 16 are a bottom side LB defined as the length of the bore between the bottom hinges of the sides L1 and L2, and a top side LT defined as the length of the patient support 14 between the top hinges of the sides L1 and L2. The two sides LB and LT are of equal length. Thus, opposite sides of the parallelogram are equal in length, that is, L1=L2 and LB=LT. Euclidean geometry dictates that a consequence of this arrangement is that the angles of the two sides L1 and L2 relative to the plane of LB (or, equivalently, relative to the plane of LB) are also equal, and that sides LB and LT remain parallel as the patient support 14 is lifted by the motorized support pedestal 24 via the bed extension 22. Furthermore, these geometrical relationships enforced by the mechanical linkage 16 provides for structural rigidity under the upward force applied at a single end of the patient support 14 by the bed extension 22.

In most imaging examination tasks, it is beneficial for the patient support 14 to remain parallel with the bottom of the bore 5, and hence level, as it is raised up by the lifted by the motorized support pedestal 24 via the bed extension 22. This is achieved by the illustrated mechanical linkage 16. However, it is further recognized herein that a gradual tilting of the patient support could be obtained by making sides L1 and L2 of different lengths (variant not illustrated), with the difference in the lengths controlling the rate of tilting as the patient support 14 is lifted. In this variant case the linkage can still be a Scott Russell linkage. It is contemplated that there could be clinical applications for this contemplated variant case, such as tilting the patient, so the feet are elevated relative to the head to promote blood flow toward the head in certain magnetic resonance angiography (MRA) examinations. The bed 20 should also be tilted, otherwise there will not be a smooth transfer of the tabletop 26 from the bed 20 to the patient support 14.

Advantageously, the bed extension 22 allows for automatic vertical alignment of the patient support 14 of the bridge 12 and the tabletop 26 resting on the bed 20 as the bed 20 is raised by the bed support pedestal 24. Therefore, installation tolerances for such a vertical alignment can become less strict. Moreover, no additional sensors and controllers are needed to align the horizontal guidance of the tabletop 26 with the bridge 12.

It should also be noted that the bed extension 22 does not need to be integral with the bed 20. For example, the bed extension 22 could be a metal bracket or the like that is bolted or otherwise fastened to the bed 20. Alternatively, the bed extension 22 could be integral with the bed, e.g., if the bed 20 is a molded plastic pallet the bed extension 22 could be integrally formed during the molding as a molded plastic extension. Moreover, the bed extension 22 may comprise two (or more) individual extensions, e.g., a left bed extension (e.g., a left rod) extending underneath a left side of the tabletop 14 of the bridge 12 and a right bed extension (e.g., a right rod) extending underneath a right side of the tabletop 14 of the bridge 12.

Figure 4:
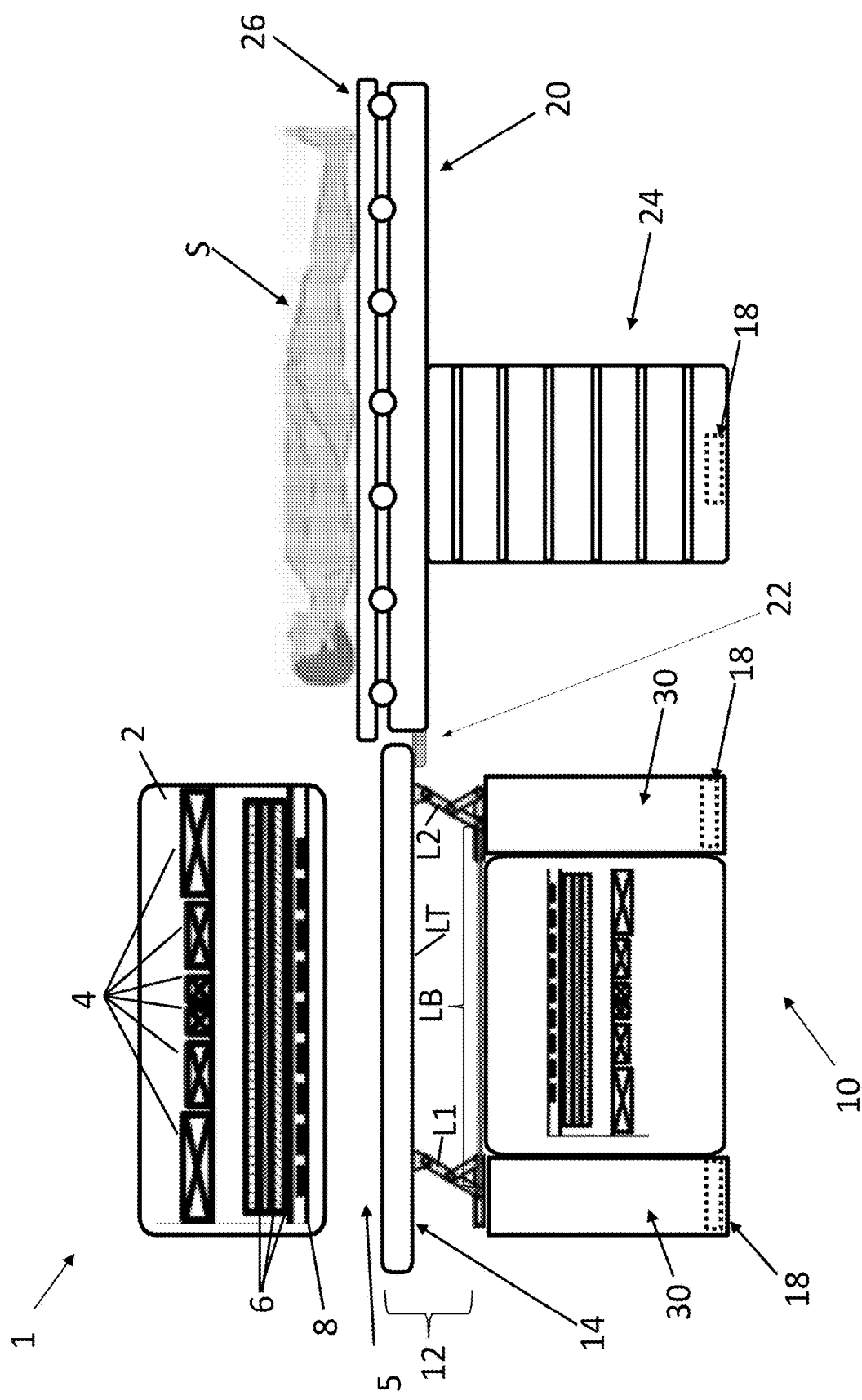
FIGS. 4-7 show alternate embodiments of the patient transfer system of FIG. 1.

FIGS. 4-7 show alternate embodiments of the patient transfer system 10. FIG. 4 shows an embodiment of the patient transfer system 10 that includes pedestals 30 disposed on opposing ends of the housing 2 along a longitudinal axis thereof. The pedestals 30 can include the motor 18 (shown as two motors in FIG. 4) for controlling vertical movement of the bridge 12. That is, the motors 18 operate to lift the mechanical linkage 16 to lift the patient support 14. Advantageously, the pedestals 30 also provide in an additional decoupling of the bridge 12 from the magnet 4, which is likely to reduce the vibrations felt by the subject S coming from the magnet 4. In this embodiment, the mechanical linkage 16 secures the patient support 14 in the bore 5 of the imaging device 1 by way of hinged connections of the sides L1 and L2 to the respective pedestals 30. As indicated in FIG. 4, in this embodiment the bottom side LB is the length between the bottom hinges connecting the sides L1 and L2 to the respective pedestals 30, and again LB=LT to provide a parallelogram four-bar linkage.

Figure 5:
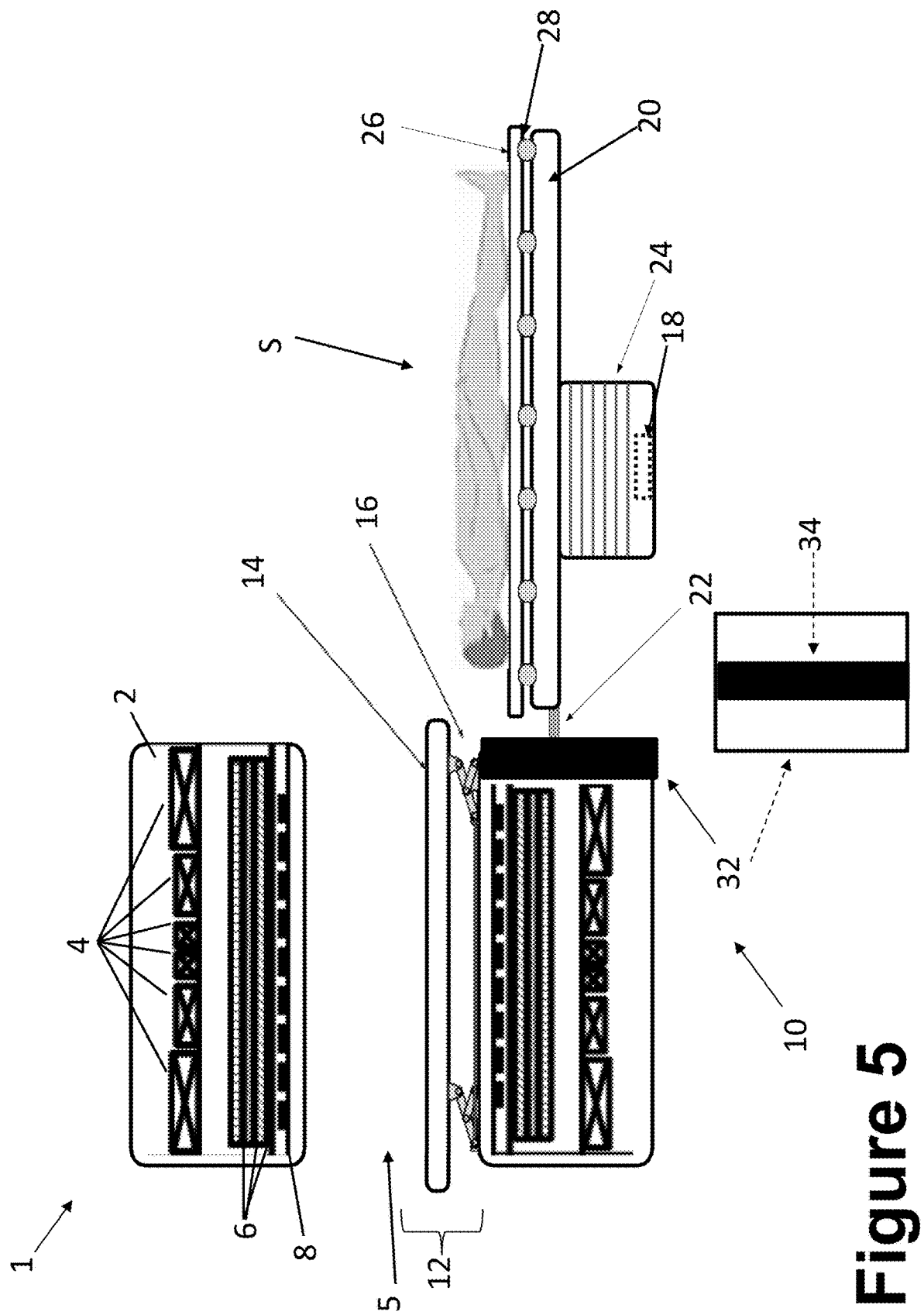

FIG. 5 shows an embodiment of the patient transfer system 10 that includes a cover 32. In some examples, while the tabletop 26 is moving upwards while outside of the bore 5, a gap between the tabletop 26 and the bridge 12 will be decreasing, which can create a finger-pinching hazard. To eliminate this gap, the cover 32 is secured to the bridge 12 and is disposed adjacent the MR device 1. As shown in FIG. 5, the cover 32 includes one or more vertical slots 34 in which the bed extension 22 can be disposed. Then bed extension 22 then moves within the slot 34 during movement of the tabletop 26. In some examples, the cover 32 can be added to the embodiment of the patient transfer system 10 shown in FIG. 4 (i.e., with the pedestals 32).

Figure 6:
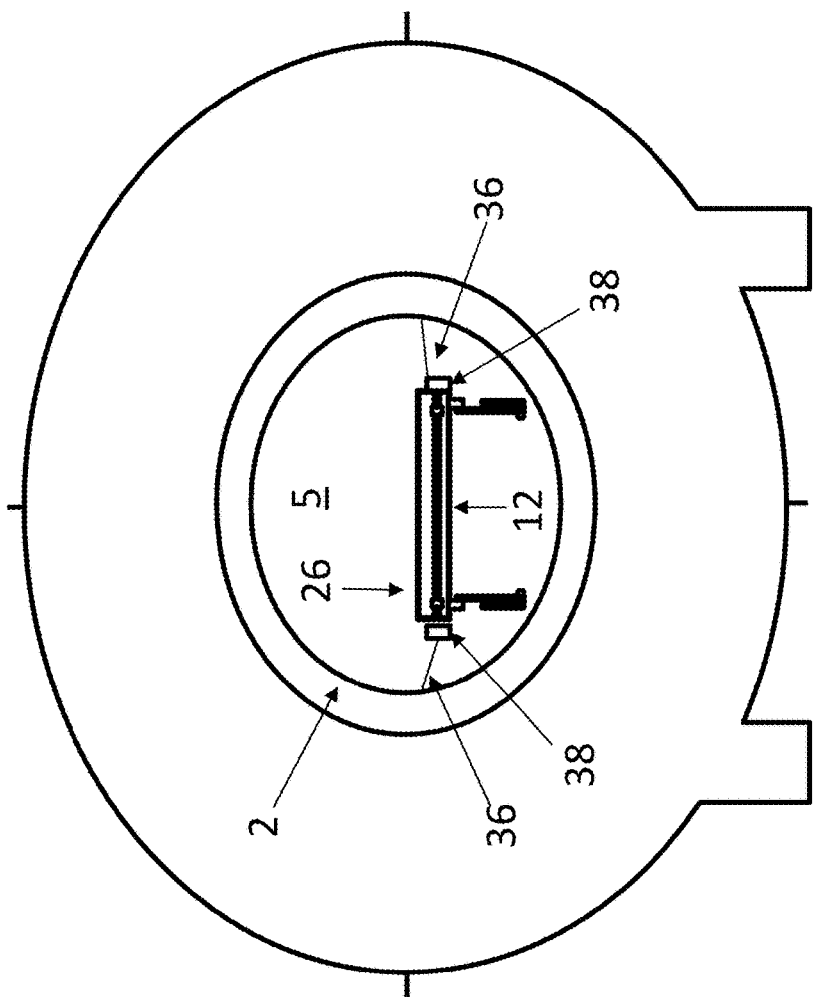

FIG. 6 is a rear view of the MR system 1, and includes one or more side skirts 36 secured by hinges 38 to a portion (i.e., a side wall) of the housing 2 that defines the bore 5. The side skirts 36 extend between sides of the bridge 12 and the side wall of the housing 2. In some examples, a gap between the tabletop 26 and the sidewall of the bore 5 can create another potentials finger-pinching gap locations. The skirts 36 are provided to eliminate these gaps. In lieu of skirts 36, other mechanicals such as sliding covers can be provided.

Figure 7:
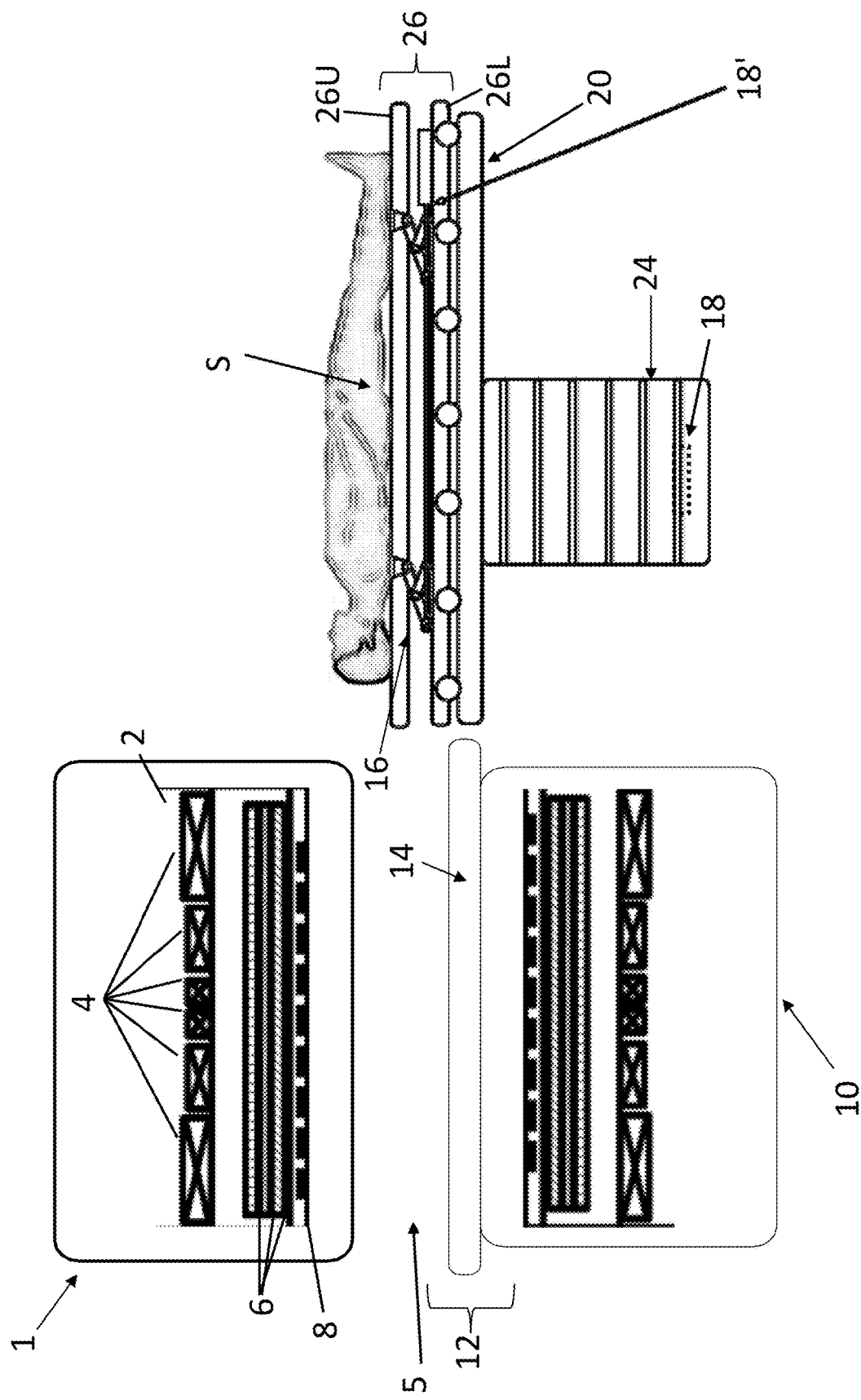

FIG. 7 shows a different embodiment of the patient transfer system 10 in which the patient support 14 in the bore 5 is fixed (i.e., not height-adjustable), and instead the mechanical linkage 16 is integrated into the tabletop 26 that is rolled or slid between the bed 20 located outside of the bore 5 and the patient support 14 in the bore 5. To this end, the tabletop 26 of previously described embodiments is modified to from a modified tabletop 26 as shown in FIG. 7, in which the tabletop 26 comprises an upper tabletop 26U on which the subject S is directly placed, and a lower tabletop 26L disposed underneath the upper tabletop 26U. The mechanical linkage 16 in this embodiment connects the lower and upper tabletops 26U and 26L. In this design, the motor 18 of the motorized bed support pedestal 24 cannot operate the mechanical linkage 16. Instead, a separate motor 18' (or motorized actuator 18') is integrated into the patient support to lift the upper tabletop 26U relative to the lower tabletop 26L under constraint imposed by the mechanical linkage 16. In this embodiment, the separation between the upper and lower tabletops 26U, 26L is typically set via the motor 18' prior to the tabletop 26 being rolled or slid from the bed 20 located outside of the bore 5 onto the (here fixed-height) patient support 14 in the bore 5.

With reference to FIG. 8, and with continuing reference to FIGS. 1-7, an illustrative MR method 100 using the MR device 1 is diagrammatically shown as a flowchart. To begin the method 100, the bridge 12 is secured within the bore 5 via the mechanical linkage 16. At an operation 102, the bed support pedestal 24 is operated with the motor 18 to raise the bed 20. At an operation 104, the motorized operation of the bed support pedestal 24 is ceased when the bed extension 22 contacts the patient support 14. At an operation 106, the tabletop 26 is rolled or moved into the bore 5 and on top of the patient support 14. At an optional operation 108, the tabletop 26 is positioned within the bore 5 with the skirts 36 to eliminate gaps between the sidewalls of the bore 5 and the tabletop 26.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus, comprising:
   a bridge,
      wherein the bridge comprises a patient support and a mechanical linkage,
      wherein the patient support is arranged to be disposed in a bore of an imaging device;
   a bed disposed adjacent the imaging device,
      wherein the bed has a bed extension,
      wherein the bed extension is arranged to extend beneath the patient support;
   a tabletop,
      wherein the tabletop is arranged to support a patient disposed thereon, wherein the tabletop is configured to be moved from a first position, disposed on top of the bed, to a second position, disposed on top of the patient support, to move the patient at least partially within the bore;
a bed support pedestal,
wherein the bed support pedestal is arranged to provide motorized height adjustment of the bed,
wherein motorized operation of the bed support pedestal raises the bed,
wherein motorized operation of the bed support pedestal also lifts the patient support via the bed extension which extends beneath the patient support,
wherein the side cover is secured to at least a portion of the bridge,
wherein the side cover is disposed alongside the imaging device,
wherein the side cover includes at least one vertical slot in which the bed extension is disposed,
wherein the bed extension is arranged to move vertically within the vertical slot during the motorized operation of the bed support pedestal.

2. The apparatus of claim 1, wherein the mechanical linkage of the bridge is a Scott Russell linkage.

3. The apparatus of claim 1, wherein the bridge does not include a motor.

4. The apparatus of claim 1, further comprising:
at least one side skirt disposed in the bore of the imaging device,
wherein the at least one side skirt is secured by at least one hinge to at least one side of the bridge,
wherein the at least one side skirt extends between the at least one side of the bridge and a surface of a housing of the imaging device, wherein the surface defines the bore.

5. The apparatus of claim 1, further comprising the imaging device,
wherein the imaging device is a magnetic resonance (MR) imaging device.

6. The apparatus of claim 1, further comprising further comprising the imaging device,
wherein the imaging device comprises a magnetic resonance (MR) imaging device.

7. The apparatus of claim 1, wherein the mechanical linkage is disposed within the bore, wherein the mechanical linkage is attached to a surface of a housing of the imaging device, wherein the surface defines the bore.

8. The apparatus of claim 1, further comprising two pedestals, wherein the two pedestals disposed on opposing ends of a housing of the imaging device along a longitudinal axis thereof, wherein the mechanical linkage is attached to each of the two pedestals.

9. The apparatus of claim 8, wherein each of the two pedestals disposed on opposing ends of a housing of the imaging device has a corresponding motor, wherein the motors are arranged to control a vertical movement of the bridge.

10. An apparatus, the apparatus comprising:
a bed, wherein the bed is disposed adjacent an imaging device and the bed has a bed extension;
a bed support pedestal, wherein the bed support pedestal is arranged to provide motorized height adjustment of the bed;
a tabletop,
wherein the tabletop is arranged to support a patient disposed thereon,
wherein the tabletop is arranged to be rolled or slid from the bed disposed adjacent the imaging device onto a patient support disposed at least partially within a bore of the imaging device while a patient is disposed on the tabletop to convey the patient disposed on the tabletop at least partially into the bore;
a mechanical linkage configured to adjust a height of the patient on the tabletop in the bore of the imaging device, wherein the mechanical linkage is connected with the patient support;
a motor operatively connected to operate the mechanical linkage; and
a side cover disposed alongside the imaging device,
wherein the side cover includes at least one vertical slot in which the bed extension is disposed,
wherein the bed extension is arranged to move vertically within the vertical slot during a motorized operation of the bed support pedestal.

11. The apparatus of claim 10, wherein the tabletop comprises:
an upper tabletop portion; and
a lower tabletop portion,
wherein the mechanical linkage is secured between the upper tabletop portion and the lower tabletop portion; and
wherein the motor is connected to operate the mechanical linkage to lift the upper tabletop portion respective to the lower tabletop portion.

12. The apparatus of claim 10,
the bed extending extends underneath the patient support disposed in the bore; and
wherein the motor comprises a motor of the bed support pedestal, wherein operation of the motor of the bed support pedestal to raise the bed also lifts the patient support and the bed extension.

13. The apparatus of claim 12, further comprising: at least one side skirt,
wherein the at least one side skirt is disposed in the bore of the imaging device and secured by hinges to the sides of the patient support,
wherein the at least one side skirt extends sides of the patient support and a surface of a housing of the imaging device, wherein the surface defines the bore.

14. The apparatus of claim 10, wherein the mechanical linkage is a Scott Russell linkage.

15. An imaging method, comprising:
operating a bed support pedestal to raise a bed disposed adjacent an imaging device, wherein the bed has a bed extension;
ceasing the operating of the bed support pedestal when the bed extension extends underneath a patient support and contacts the patient support,
wherein the patient support is at least partially disposed in a bore of the imaging device,
wherein the patient support is secured in the bore by a mechanical linkage,
wherein raising the bed also lifts the patient support via the bed extension which extends underneath the patient support; and
rolling or sliding a tabletop from the bed disposed adjacent the imaging device onto the patient support disposed at least partially within the bore,
wherein a side cover is disposed adjacent the imaging device,
wherein the side cover includes at least one vertical slot in which the bed extension and the bed extension moves vertically within the vertical slot during a motorized operation of the bed support pedestal.

16. The method of claim 15, wherein the mechanical linkage is a Scott Russell linkage.

17. The method of claim 15, wherein the patient support and the mechanical linkage comprise a bridge, the method further comprising:
   positioning the bed within the bore of the imaging device with at least one skirt, wherein the at least one skirt is secured to the bridge, and is arranged to engage a surface of a housing of the imaging device, wherein the surface defines the bore.

18. The method of claim 15,
   wherein the patient support and the mechanical linkage comprise a bridge and the side cover is secured to a portion of the bridge.

* * * * *